United States Patent
Kuo et al.

(10) Patent No.: US 8,243,270 B2
(45) Date of Patent: *Aug. 14, 2012

(54) VIBRATING TIP SURFACE ENHANCED RAMAN SPECTROSCOPY

(75) Inventors: Huei Pei Kuo, Cupertino, CA (US); Michael J. Stuke, Palo Alto, CA (US); Min Hu, Sunnyvale, CA (US); Fung Suong Ou, Palo Alto, CA (US); Shih-Yuan (SY) Wang, Palo Alto, CA (US); Alexandre M. Bratkovski, Mountain View, CA (US); Wei Wu, Palo Alto, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 363 days.

This patent is subject to a terminal disclaimer.

(21) Appl. No.: 12/697,156

(22) Filed: Jan. 29, 2010

(65) Prior Publication Data

US 2011/0188035 A1 Aug. 4, 2011

(51) Int. Cl.
*G01J 3/44* (2006.01)

(52) U.S. Cl. ........................................... 356/301

(58) Field of Classification Search ............... 356/301
See application file for complete search history.

(56) References Cited

U.S. PATENT DOCUMENTS

| | | | |
|---|---|---|---|
| 7,609,377 B2 | 10/2009 | Wu et al. | |
| 7,639,355 B2 * | 12/2009 | Fattal et al. | 356/301 |
| 7,696,477 B2 * | 4/2010 | Sigalas et al. | 250/306 |
| 2003/0124717 A1 * | 7/2003 | Awano et al. | 435/287.2 |
| 2006/0252065 A1 | 11/2006 | Zhao et al. | |
| 2007/0166539 A1 | 7/2007 | Zhao et al. | |
| 2011/0188034 A1 * | 8/2011 | Stuke et al. | 356/301 |

OTHER PUBLICATIONS

Clement Yuen et al., "Surface-Enhanced Raman Scattering: Principles, Nanostructures, Fabrications, and Biomedical Applications," Journal of Innovative Optical Health Sciences, vol. 1, No. 2, 2008, pp. 267-284.
J. L. Yao et al., "A complementary study of surface-enhanced Raman scattering and metal nanorod arrays," Pure Appl. Chem., vol. 72, No. 1, 2000, pp. 221-228.
Ralph A. Tripp et al., "Novel nanostructures for SERS biosensing," Nanotoday, vol. 3, No. 3-4, Jun.-Aug. 2008, pp. 31-37.
Motofumi Suzuki et al., "In-line aligned and bottom-up Ag nanorods for surface-enhanced Raman spectroscopy," Applied Physics Letters, vol. 88, 2006, pp. 203121-1 to 203121-3.

* cited by examiner

*Primary Examiner* — Layla Lauchman

(57) ABSTRACT

A vibrating tip surface enhanced Raman spectroscopy (SERS) apparatus, system and method employ a nano-needle configured to vibrate. The apparatus includes the nano-needle with a substantially sharp tip at a free end opposite an end attached to a substrate. The tip is configured to adsorb an analyte. The apparatus further includes a vibration source configured to provide an alternating current (AC) electric field that induces a vibration of the free end and the tip of the nano-needle. Vibration of the nano-needle under the influence of the AC electric field facilitates detection of a Raman scattering signal from the analyte adsorbed on the nano-needle tip. The system further includes a synchronous detector configured to be gated cooperatively with the vibration of the nano-needle. The method includes inducing the vibration, illuminating the vibrating tip to produce a Raman signal, and detecting the Raman signal using the detector.

20 Claims, 5 Drawing Sheets

VIBRATING TIP SURFACE ENHANCED RAMAN SPECTROSCOPY

STATEMENT REGARDING FEDERALLY SPONSORED RESEARCH OR DEVELOPMENT

This invention has been made with government support under Contract No. HR0011-09-3-0002, awarded by Defense Advanced Research Projects Agency. The government has certain rights in the invention.

CROSS-REFERENCE TO RELATED APPLICATIONS

N/A

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (e.g., visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman-scattering.

Raman-scattering optical spectroscopy employs an emission spectrum or spectral components thereof produced by inelastic scattering of photons by an internal structure of the material being illuminated. These spectral components contained in a response signal (e.g., a Raman signal) may facilitate determination of the material characteristics of an analyte species including identification of the analyte.

Unfortunately, the Raman signal produced by Raman-scattering is extremely weak in many instances compared to elastic or Rayleigh scattering from an analyte species. The Raman signal level or strength may be significantly enhanced by using a Raman-active material (e.g., Raman-active surface), however. For example, a surface that includes a Raman-active material may be employed in surface enhanced Raman-scattering (SERS) optical spectroscopy to significantly enhance a signal level or intensity of the Raman signal produced by a particular analyte species. While SERS has proven to yield good results in many applications, further improvements are still being sought.

For example, SERS often suffers from or exhibits unpredictable hot spots across the surface. The hot spots produce much higher-level Raman signals than surrounding areas but the location and quantity of these hot spots can be difficult to control. As such, it is often necessary to flood the entire surface with analyte to insure that sufficient analyte reaches the hot spots and produces a detectable Raman signal. Requiring the surface to be flooded precludes detection of very small amounts of analyte (e.g., single molecules) and also hinders identifying other analyte characteristics such as species distribution within a sample.

Attempts to localize or control the production of hot spots have included the use of sharp tips in conjunction with a SERS surface in what is known as tip enhanced Raman spectroscopy (TERS). In TERS, a sharp, conductive tip is placed very close to but spaced apart from the SERS surface. The tip acts as an antenna concentrating and locally enhancing the electromagnetic field in a region between the tip and the surface. While producing results including detection of extremely small quantities of analyte, TERS presents many practical challenges to implementation and use.

BRIEF DESCRIPTION OF THE DRAWINGS

The various features of embodiments of the present invention may be more readily understood with reference to the following detailed description taken in conjunction with the accompanying drawings, where like reference numerals designate like structural elements, and in which.

Figure 1:
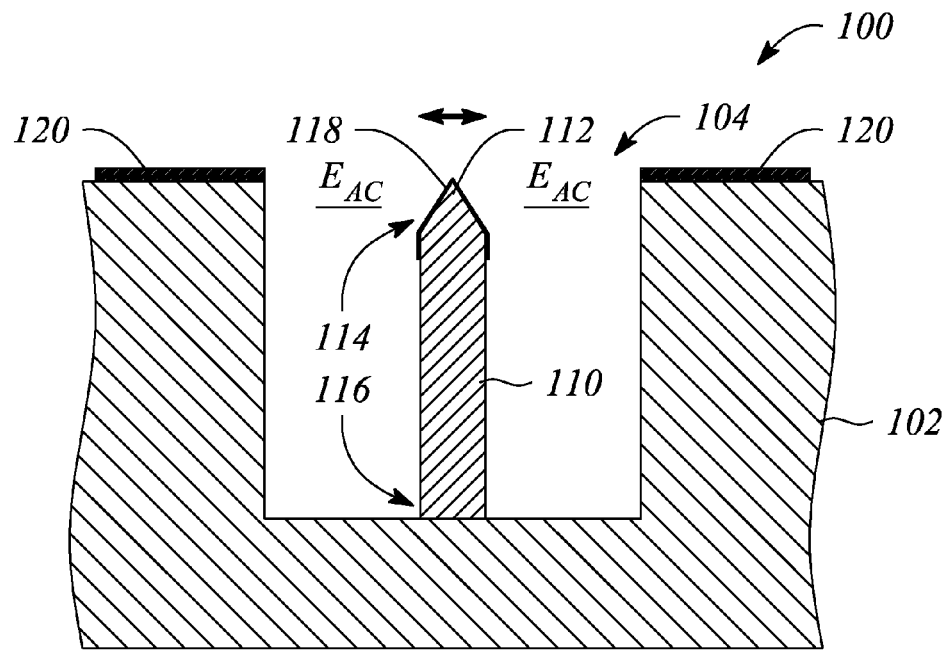
FIG. 1 illustrates a cross sectional view of a vibrating tip surface enhanced Raman spectroscopy (SERS) apparatus, according to an embodiment of the present invention.

Certain embodiments of the present invention have other features that are one of in addition to and in lieu of the features illustrated in the above-referenced figures. These and other features of the invention are detailed below with reference to the preceding drawings.

DETAILED DESCRIPTION

Embodiments of the present invention provide surface enhanced Raman spectroscopy (SERS). In particular, SERS is performed on or in a vicinity of a tip of a nano-needle, according to various embodiments of the present invention. In some embodiments, the tip of the nano-needle is substantially sharp and may enhance a signal strength of a Raman signal produced by Raman scattering from an analyte. In some embodiments, the analyte is adsorbed on the tip and the tip enhances the Raman signal of the adsorbed analyte. Further, various embodiments of the present invention employ vibration of the tip, the vibration being induced by a varying or alternating current (AC) electric field acting on the nano-needle in a vicinity of the tip. The tip vibration facilitates detection of the Raman signal by improving a signal-to-noise ratio (SNR) of the Raman signal at or within a detector. Specifically, a synchronous detector may be employed to detect the Raman signal where the detector is synchronized to a vibration frequency of the vibrating tip.

Embodiments of the present invention employ a vibrating tip of a nano-needle to enhance production and detection of a Raman signal from an analyte. A 'nano-needle' herein is defined as an elongated, nanoscale structure having a length that exceeds by more than several times a nanoscale cross sectional dimension (e.g., width) taken in a plane perpendicular to the length (e.g., length>10× width). In general, the length is much greater than the width or cross sectional dimension to facilitate inducing a vibration of the tip of the nano-needle. In some embodiments, the length (or height) exceeds the cross sectional dimension (or width) by more than a factor of 5 or 10. For example, the width may be about 40 nanometers (nm) and the height may be about 400 nm. In another example, the width at a base of the nano-needle may be between 20 nm and 100 nm and the length may be more than about a 1 micrometer (μm). In another example, the nano-needle may be conical with a base having a width of between 100 nm and 500 nm and a length or height that between one and several micrometers.

In various embodiments, the nano-needle may be grown (i.e., produced by an additive process) or produced by etching or a similar subtractive process. For example, the nano-needle may be grown as a nanowire using a vapor-liquid-solid (VLS) growth process. In another embodiment, the nano-needle may be produced by using an etching process such as, but not limited to, reactive ion etching, to remove surrounding material leaving behind the nano-needle. Various techniques used in the fabrication of micro-electromechanical systems (MEMS) and nano-electromechanical systems (NEMS) are applicable to the fabrication of the nano-needle.

Further, as used herein, the article 'a' is intended to have its ordinary meaning in the patent arts, namely 'one or more'. For example, 'a nano-needle' means one or more nano-needles and as such, 'the nano-needle' explicitly means 'the nano-needle(s)' herein. Also, any reference herein to 'top', 'bottom', 'upper', 'lower', 'up', 'down', 'front', back', 'left' or 'right' is not intended to be a limitation herein. Herein, the term 'about' when applied to a value generally means plus or minus 10% unless otherwise expressly specified. Moreover, examples herein are intended to be illustrative only and are presented for discussion purposes and not by way of limitation. Co-pending U.S. patent application Ser. No. 12/697,136 of Stuke et al., entitled "Surface Enhanced Raman Spectroscopy Employing Vibrating Nanorods," filed concurrently herewith, is incorporated by reference in its entirety herein.

FIG. 1 illustrates a cross sectional view of a vibrating tip surface enhanced Raman spectroscopy (SERS) apparatus 100, according to an embodiment of the present invention. In particular, the vibrating tip SERS apparatus 100 is illustrated on a substrate 102. An analyte may be introduced to and analyzed by the vibrating tip SERS apparatus 100, according to some embodiments. For example, the analyte may be introduced by flowing a gas or a liquid along a channel or trench 104 in the substrate (e.g., as illustrated). The channel 104 may enclose or otherwise house a portion of the vibrating tip SERS apparatus 100, according to some embodiments. In some embodiments, the analyte is adsorbed onto a surface of a vibrating tip of the vibrating tip SERS apparatus 100. A Raman signal produced by the adsorbed analyte is detected and analyzed to facilitate analysis (e.g., identification of) the analyte, according to some embodiments.

According to various embodiments, the vibrating tip SERS apparatus 100 comprises a nano-needle 110. As illustrated, the nano-needle 110 is attached to the substrate 102 at one end. In some embodiments, the nano-needle 110 is rigidly attached to the substrate 102. The nano-needle 110 has a tip 112 at a free end 114 that is opposite a fixed end 116 of the nano-needle 110 that is attached to the substrate 102. According to some embodiments, the tip 112 is substantially sharp. By 'sharp' it is meant that the tip 112 tapers from a cross sectional size of the nano-needle 110 to an edge or a point at an end of the tip 112. The edge or the point generally has a relatively acute angle of inflection between surfaces of the tip 112 leading up to the edge or the point. In other words, a cross sectional size of the tip 112 in a vicinity of the end of the tip 112 (i.e., the edge or the point) is much smaller than an overall cross sectional size of the nano-needle 110 away from the tip end. As such, the nano-needle 110 having a tip 112 that is substantially sharp distinguishes it from other nano-needles having rounded or flat tips.

Figure 2A:
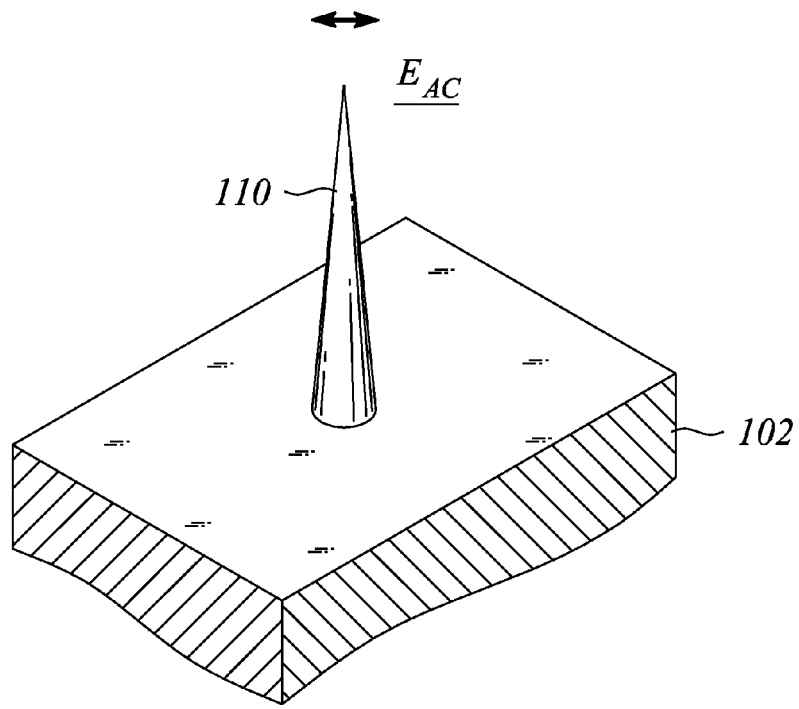
FIG. 2A illustrates a perspective view of a nano-needle having a generally tapered shape, according to an embodiment of the present invention.

In some embodiments of the present invention, the nano-needle 110 has a generally tapered shape compared to that illustrated in FIG. 1. FIG. 2A illustrates a perspective view of a nano-needle 110 having a generally tapered shape, according to an embodiment of the present invention. In particular, as illustrated in FIG. 2A, the tapered shape of the nano-needle 110 is conical. In other embodiments (not illustrated), the tapered shape may be generally faceted or pyramidal, for example having three, four, or more facets or sides. In yet other embodiments, the tapered shape may have a curvilinear perimeter when considering a cross section perpendicular to a long axis of the nano-needle 110.

In other embodiments such as that illustrated in FIG. 1, the nano-needle 110 has a columnar shape. In such embodiments, the nano-needle 110 comprises columnar portion that extends from the point of attachment to a vicinity of the free end 114 and a tapered portion at or in the vicinity of the free end 114. The tapered portion provides the substantially sharp tip 112. In particular, the nano-needle 110 having a columnar shape tapers to a substantially sharp point only in a vicinity of the tip 112 to distinguish from the tapered-shape nano-needle 110 exemplified in FIG. 2A. The columnar portion may have either curvilinear or faceted perimeter in cross section. In particular, with respect to a cross section taken in a plane perpendicular to the long axis of the nano-needle 110 and within the columnar portion, the columnar-shaped nano-needle 110 may have a cross section that is characterized by either a curvilinear perimeter or a polygonal perimeter. For example, the columnar-portion may have a triangular cross section, a rectangular cross section or a cross section with more than four sides. In another example, the columnar portion may have a perimeter that is circular, oval or similarly curvilinear (e.g., a square with rounded corners).

Figure 2B:
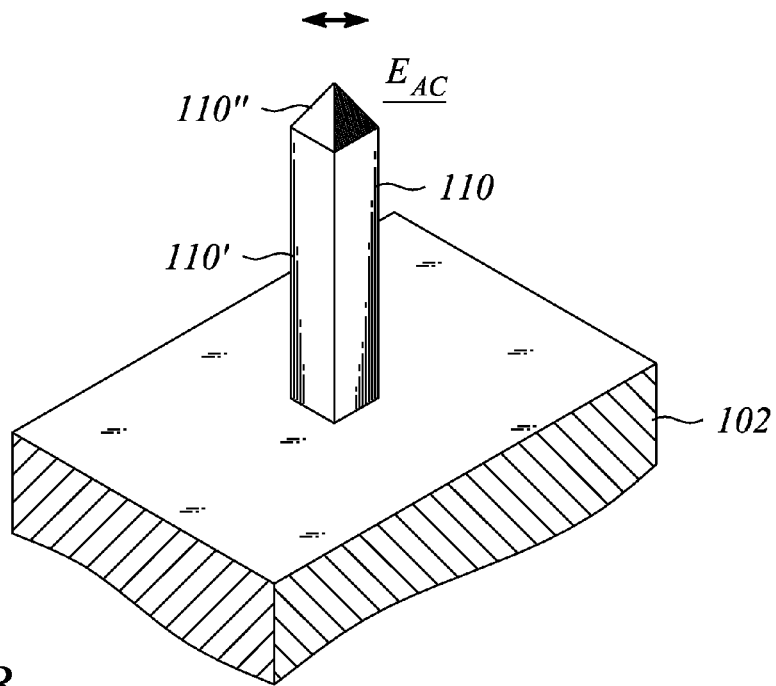
FIG. 2B illustrates a perspective view of a columnar-shaped nano-needle, according to another embodiment of the present invention.

FIG. 2B illustrates a perspective view of a columnar-shaped nano-needle 110, according to another embodiment of the present invention. A columnar portion 110' of the columnar-shaped nano-needle 110 extends from the substrate to near the tip 112. In the vicinity of the tip 112, the columnar portion 110' is replaced by or gives way to the tapered portion 110", as illustrated in FIG. 2B. As illustrated, the columnar-shaped nano-needle 110 has a rectangular cross section within the columnar portion 110' and tapers to a four-sided pyramidal shaped within the tapered portion 110".

The nano-needle 110, whether tapered or columnar, generally has a long narrow profile that extends up from the attachment point to the substrate 102. The long narrow shape facilitates inducing vibration of the tip 112 which is described below. In particular, the nano-needle 110 may be greater than about 5 times as long as it is wide (or thick), according to some embodiments. In some embodiments, the nano-needle 110 may be greater than five to ten times as long as it is wide. For example, the nano-needle 110 may have a width between several nanometers (nm) and about 100 nm and a length that is between 500 nm and 1 micron (µm).

In some embodiments, the nano-needle 110 comprises a Raman-active material. By definition herein, a Raman-active material is a material that facilitates Raman scattering and the production or emission of the Raman signal from an analyte adsorbed on or in a surface layer of the material during Raman spectroscopy. Examples of Raman-active materials include, but are not limited to, gold (Au), silver (Ag), and copper (Cu). In some embodiments, the Raman-active materials comprise a layer or layers having nanoscale surface roughness. Nanoscale surface roughness is generally characterized by nanoscale surface features on the surface of the layer(s). Nanoscale surface roughness may be produced spontaneously during deposition of the Raman-active material layer(s) (e.g., gold deposition), for example.

In some embodiments, the nano-needle 110 may comprise a semiconductor. For example, the semiconductor may comprise silicon (Si) or germanium (Ge) or an alloy of Si and Ge. In other examples, the semiconductor may comprise gallium arsenide (GaAs), indium gallium arsenide (InGaAs), and gallium nitride (GaN), as well as various other III-V, II-VI, and IV-VI compound semiconductors. In some of these embodiments, the semiconductor may be doped to render the semiconductor more conductive than an intrinsic or undoped form of the semiconductor. For example, the Si may be doped with phosphorus (P), an n-type dopant, or boron (B), a p-type dopant, to increase the conductivity. Increasing the conductivity of the semiconductor within the nano-needle 110 may facilitate inducing vibration using an electric field which is described below, for example.

Referring back to FIG. 1, in some embodiments, the nano-needle 110, or at least a portion thereof, is coated with a layer 118 of Raman-active material. For example, the nano-needle 110 may be coated with a layer 118 of metal such as, but not limited to, gold (Au), silver (Ag) or copper (Cu) since these metals are know as Raman-active materials in conventional SERS. In some embodiments, the layer 118 of Raman-active material is relatively thin compared to a width or thickness of the nano-needle 110. For example, the Raman-active material layer 118 may have a width that is less than about 1/10 of the width of the nano-needle 110. The Raman-active material layer 118 may be approximately 5-10 nm wide, for example.

In some embodiments, the Raman-active material layer 118 may be confined to or localized in a vicinity of the tip 112, as illustrated in FIG. 1. In other embodiments, the Raman-active material layer 118 may extend along more of the nano-needle 110 than just a vicinity of the tip 112. In some embodiments, an entire length of the nano-needle 110 is coated with the Raman-active material layer 118. In some embodiments, the Raman-active material layer 118 (e.g., metal) may be annealed or otherwise treated to increase a nanoscale surface roughness of the Raman-active material layer 118 after deposition. Increasing the surface roughness may enhance Raman scattering from an adsorbed analyte, for example. In some embodiments, the Raman-active material layer 118 comprises a layer or layers of nanoparticles. For example, a monolayer of gold (Au) nanoparticles may be used to coat the nano-needle 110 and produce the Raman-active material layer 118. The layer(s) of nanoparticles may provide a nanoscale roughness that enhances Raman scattering, for example.

Figure 2C:
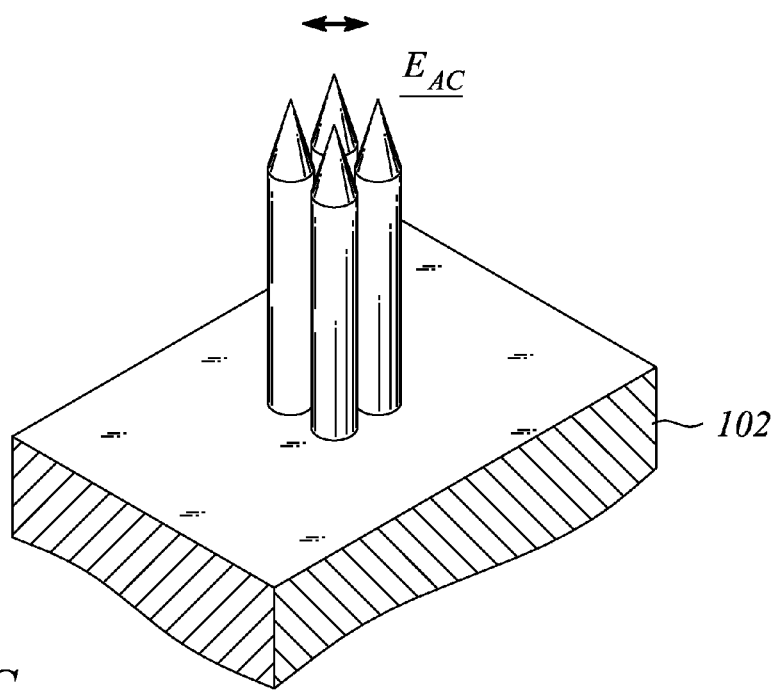
FIG. 2C illustrates a perspective view of an exemplary plurality of nano-needles arranged as a spaced apart array, according to an embodiment of the present invention.

In some embodiments, the nano-needle 110 comprises a plurality of nano-needles 110. The plurality of nano-needles 110 may be arranged in a spaced apart array, for example. FIG. 2C illustrates a perspective view of an exemplary plurality of nano-needles 110 arranged as a spaced apart array, according to an embodiment of the present invention. Also illustrated in FIG. 2C are nano-needles 110 having a columnar shape based on a circular column (i.e., having a circular cross section).

In some embodiments, a surface of the nano-needle 110 may be functionalized to facilitate adsorption of the analyte. For example, the Raman-active material layer 118 on the tip 112 (illustrated in FIG. 1) may be functionalized with a binding group to facilitate binding with a specific target analyte species. The functionalized surface may selectively bond with DNA or RNA, for example.

Referring again to FIG. 1, the vibrating tip SERS apparatus 100 further comprises a vibration source configured to provide an alternating current (AC) electric field $E_{AC}$. According to some embodiments, vibration of the nano-needle 110 under the influence of the AC electric field $E_{AC}$ may facilitate detection of a Raman signal from the analyte adsorbed on the tip 112 of the nano-needle 110. Specifically, the AC electric field $E_{AC}$ provided by the vibration source comprises an alternating or varying electric field value. The AC electric field $E_{AC}$ is characterized by a frequency and a magnitude where the frequency represents or establishes a rate at which the electric field is varying. The AC electric field $E_{AC}$ is configured to induce a vibration of the nano-needle 110 and more particularly is configured to induce a vibration of the free end 114 and the tip 112 of the nano-needle 110.

For example, the AC electric field $E_{AC}$ may comprise a pair of electric field values. A first value of the exemplary electric field $E_{AC}$ may exert a force on the free end 114 of the nano-needle 110 in a first direction (e.g., to the left). Similarly, a second value of the exemplary electric field $E_{AC}$ may exert a force on the free end 114 of the nano-needle 110 in a second direction (e.g., to the right). For example, the first value of the exemplary AC electric field $E_{AC}$ may attract charges bound within a structure of the nano-needle 110 while the second value may repel those same charges. Alternating between the first and second exemplary values in a periodic manner induces a back and forth motion of the free end 114 of the nano-needle 110 as indicated by the double-headed arrow in FIG. 1 illustrated above the nano-needle 110. The back and forth motion constitutes the induced vibration of the free end 114 and the tip 112 of the nano-needle 110.

In configuring the AC electric field $E_{AC}$ to induce vibration of the nano-needle 110, the AC electric field $E_{AC}$ may be switched abruptly between the pair of values (e.g., using a binary switching profile or a pulse train), according to some embodiments. In other embodiments, another switching profile that ranges through a plurality of electric field values may be employed such as, but not limited to, a sinusoidal profile, triangular profile or sawtooth profile. Further in configuring the AC electric field $E_{AC}$, consideration of a resonant frequency of vibration of the nano-needle 110 may be advantageously employed. In particular, selecting the frequency of the AC electric field $E_{AC}$ to correspond to a resonant frequency of the nano-needle 110 may facilitate inducing vibration.

In some embodiments, the vibration source of the vibrating tip SERS apparatus 100 comprises a pair of electrodes 120 that provide the AC electric field $E_{AC}$, as illustrated in FIG. 1. The nano-needle 110 may be disposed between the pair of electrodes 120, according to some embodiments. For example, FIG. 1 illustrates the pair of electrodes 120 on either side of the nano-needle 110. The pair of electrodes 120 is on a surface of the substrate 102 while the nano-needle 110 is located in the trench 104 between the pair of electrodes 120. Further, the tip 112 of the nano-needle 110 is adjacent to the pair of electrodes 120. Such an adjacency may increase or in some embodiments, may maximize, a magnitude of the AC electric field $E_{AC}$ at or in a vicinity of the tip 112 when compared to other orientations of the electrodes 120 and tip 112. As such, an effect that the AC electric field $E_{AC}$ provided by the pair of electrodes 120, as illustrated in FIG. 1, has on the nano-needle 110 may be increased or maximized, depending on the embodiment. In some embodiments, the AC electric field $E_{AC}$ is provided by a charge difference or an electric potential difference (e.g., a voltage difference) between the electrodes 120. In other embodiments, the potential difference is between the nano-needle 110 and one or both of the electrodes 120 of the pair.

Figure 3:
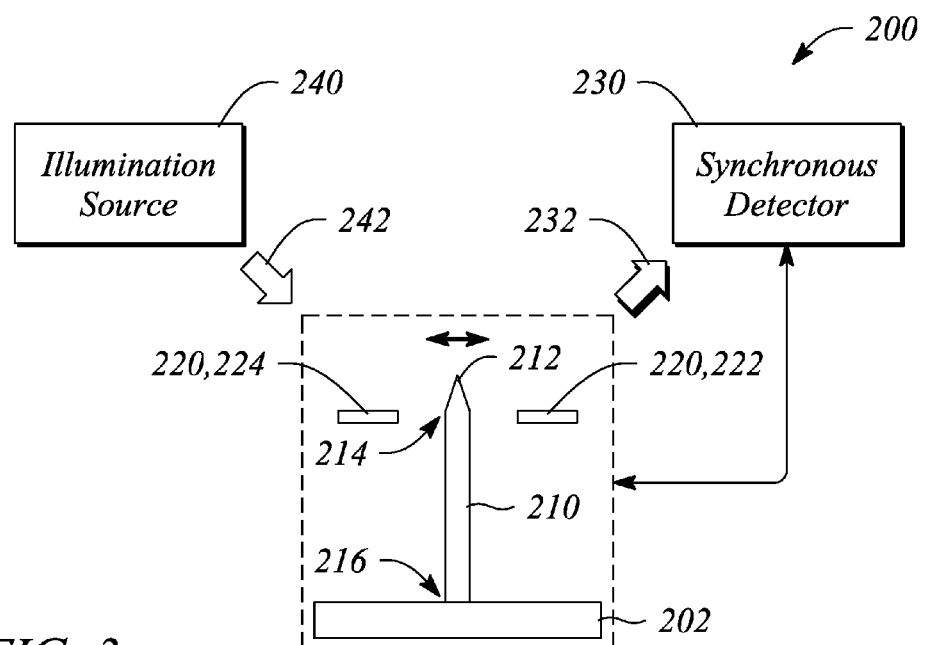
FIG. 3 illustrates a block diagram of a vibrating tip surface enhanced Raman spectroscopy (SERS) system, according to an embodiment of the present invention.

FIG. 3 illustrates a block diagram of a vibrating tip surface enhanced Raman spectroscopy (SERS) system 200, according to an embodiment of the present invention. The vibrating tip SERS system 200 comprises a nano-needle 210 being disposed between electrodes 220. In some embodiments, the nano-needle 210 is disposed between a first electrode 222 and a second electrode 224, the first electrode 222 being spaced apart from the second electrode 224, as illustrated in FIG. 3. The nano-needle 210 has a tip 212 at a free end 214. The tip 212 is substantially sharp. At a fixed end 216 opposite the free end 214, the nano-needle 210 is attached to a substrate 202. The rigid attachment of the nano-needle 210 to the substrate 202 enables the free end 214 of the nano-needle 210 to vibrate. The vibration has a resonance frequency determined by characteristics (length, mass, stiffness, etc.) of the nano-needle 210. The electrodes 220 are configured to cooperatively provide the alternating current (AC) electric field. In turn, the provided AC electric field is configured to induce a vibration of the nano-needle tip 212. In some embodiments, the nano-needle 210 and electrodes 220 are substantially similar to the nano-needle 110 and pair of electrodes 120, respectively, described above with respect to the vibrating tip SERS apparatus 100.

As illustrated in FIG. 3, the vibrating tip SERS system 200 further comprises a synchronous detector 230. The synchronous detector 230 is configured to receive a Raman signal 232 from an analyte adsorbed on the tip 212 of the nano-needle 210. In particular, the synchronous detector 230 is gated cooperatively with the vibration of the nano-needle tip 212. Cooperatively gating the synchronous detector 230 with the vibration may improve a signal-to-noise ratio (SNR) of the received Raman signal, according to some embodiments.

In particular, as the tip 212 of the nano-needle 210 vibrates, an angle of Raman scattering from the analyte will vary, according to some embodiments. As a result, an intensity or magnitude of the Raman signal 232 received by the synchronous detector 230 will vary as a function of the vibration. In other embodiments, an effective spot size (i.e., illumination extent) of the electromagnetic signal 242 produced by the illumination source 240 may be predetermined to be comparable to a vibrational amplitude (e.g., a maximum positional deviation) of the nano-needle 210. For example, a spot size of the optical signal 242 produced by the laser 240 may be adjusted by focusing optics to coincide with an expected vibrational amplitude based on a strength of the AC electromagnetic field. In such embodiments, the Raman signal magnitude will vary as the nano-needle 210 moves in an out of a central region of the illuminating electromagnetic signal 242. For example, the Raman signal 232 may switch ON and OFF as the nano-needle passes in an out of the exemplary optical signal 242 provided by the focused laser 230. In turn, a magnitude of the Raman signal 232 received by the detector 230 will vary. Cooperatively gating the synchronous detector 230 to coincide with a maximum received magnitude of the Raman signal 232 may maximize the SNR relative to a background signal, for example. FIG. 3 illustrates a connection (i.e., a lead line with double headed arrow) between the synchronous detector 230 and a combination of the nano-needle 210 and electrodes 220 to emphasize the cooperative nature of the gating of the synchronous detector 230.

In some embodiments, the vibrating tip SERS system 200 further comprises a voltage source (not illustrated). The voltage source is connected to the electrodes 220 to provide the AC electric field. For example, the voltage source may provide an alternating current (AC) voltage to the electrodes 220. In some embodiments, the voltage may be connected between the electrodes and the nano-needle 210. In embodiments that employ a voltage source, the synchronous detector 230 may be synchronized to the voltage source. In some embodiments, the AC voltage may be communicated to the synchronous detector 230 (e.g., via a connection such as is illustrated in FIG. 3) to facilitate the cooperative gating.

According to some embodiments, the vibrating tip SERS system 200 further comprises an illumination source 240. The illumination source 240 provides an electromagnetic signal 242 that illuminates the analyte adsorbed on the tip 212 of the nano-needle 210. The illumination causes Raman scattering and stimulates production of the Raman signal 232. The illumination source 240 may be a laser 240 that illuminates the tip 212 with an optical signal 242, for example.

In some embodiments, a frequency of the electromagnetic signal 242 is varied during analyte illumination. For example, an optical frequency of the laser 240 may be scanned or chirped across a band of frequencies. In another example, the electromagnetic signal 242 may be pulsed to produce a broadband signal. For example, the illumination source 240 may produce an electromagnetic signal 242 comprising a pulse train, pulses within the pulse train having a repetition frequency $f_{rep}$. The exemplary repetition frequency $f_{rep}$ may be related to a frequency $f_{ac}$ of the AC electric field. For example, the repetition frequency $f_{rep}$ of the pulse train may be four (4) times the AC electric field frequency $f_{ac}$ (i.e., $f_{rep}=4 \cdot f_{ac}$).

Figure 4:
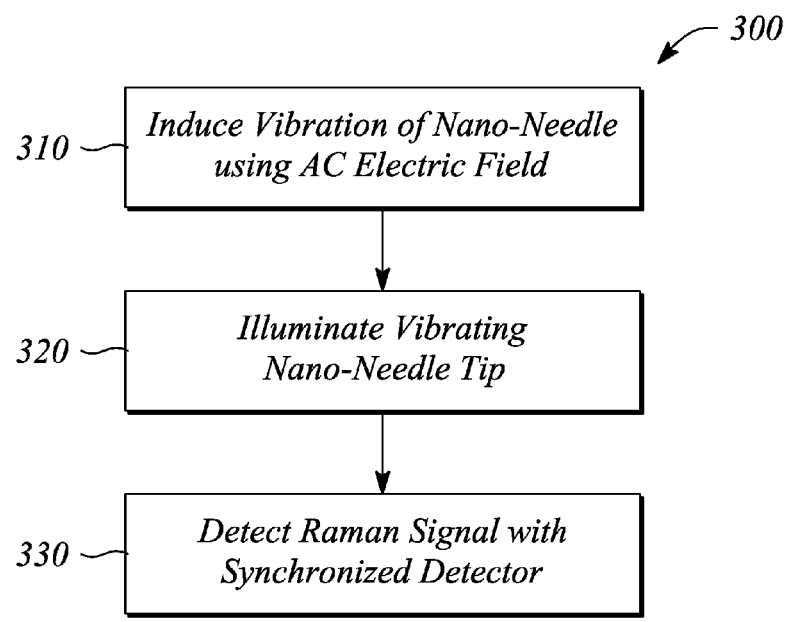
FIG. 4 illustrates a flow chart of a method of surface enhanced Raman spectroscopy (SERS), according to an embodiment of the invention.

FIG. 4 illustrates a flow chart of a method 300 of surface enhanced Raman spectroscopy (SERS), according to an embodiment of the invention. The method 300 of SERS comprises inducing 310 a vibration of a nano-needle using an alternating current (AC) electric field. According to some embodiments, the nano-needle has a tip at a free end opposite an end of the nano-needle that is attached to a substrate. In some embodiments, the tip is substantially sharp. In some embodiments, a pair of electrodes provides the AC electric field. For example, the pair of electrodes may be disposed on either side of the nano-needle in a vicinity of the tip. In some embodiments, the nano-needle is substantially similar to the nano-needle described above with respect to the vibrating tip SERS apparatus 100.

In particular, in some embodiments, the nano-needle comprises a tapered shape, the nano-needle being widest at the end of the nano-needle adjacent to the substrate and tapering to a substantially sharp point at the tip. Further, in some embodiments, the tip of the nano-needle comprises a Raman-active material coating or layer. In some of these embodiments, the Raman-active material layer comprises a conductive metal. For example, the conductive metal of the Raman-active material layer may comprise one or more of gold (Au), silver (Ag) and copper (Cu). In some embodiments, the Raman-active material layer may comprise nanoparticles of the Raman-active material (e.g., gold or silver).

In some embodiments, the nano-needle comprises Raman-active material. In some embodiments, the nano-needle comprises a semiconductor. For example, the nano-needle may comprise one or more of silicon (Si), germanium (Ge), an alloy of Si and Ge, gallium arsenide (GaAs), titanium oxide (TiO), tin oxide (SnO), indium gallium arsenide (InGaAs), and gallium nitride (GaN), as well as various other III-V, II-VI, and IV-VI compound semiconductors.

The method 300 of SERS further comprises illuminating 320 the vibrating tip of the nano-needle. In some embodiments, the illumination produces a Raman signal from an analyte adsorbed on the vibrating tip. The illumination 320 may be provided by an electromagnetic signal source (e.g., a laser), for example. The Raman signal is produced by Raman scattering by the analyte. In some embodiments, the tip enhances an electromagnetic field strength to increase a strength of the Raman signal produced by the illuminated analyte.

The method 300 of SERS further comprises detecting 330 the Raman signal. In some embodiments, detecting 330 the Raman signal comprises using a detector that is synchronized to the induced 310 vibration of the nano-needle. In particular, characteristics of the detector may be synchronized to a frequency of the induced 310 vibration. For example, the detector may be gated in a manner that corresponds to a maximum or near maximum in a received Raman signal associated with an angular variation between the detector and the vibrating tip caused by the induced 310 vibration.

FIGS. 5A-5E illustrate stages of fabrication of a vibrating tip SERS apparatus 400, according to an embodiment of the present invention. The vibrating tip SERS apparatus 400 (illustrated in FIGS. 5D-5E) may be substantially similar to the vibrating tip SERS apparatus 100, for example.

Figure 5A:
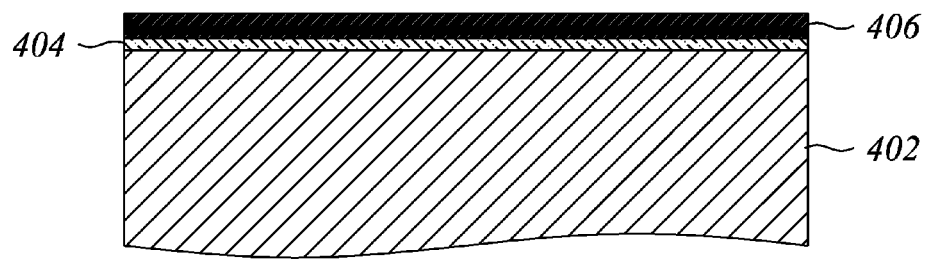
FIG. 5A illustrates a cross sectional view through a substrate at a beginning of fabrication, according to an embodiment of the present invention.

FIG. 5A illustrates a cross section through a substrate 402 at a beginning of fabrication, according to an embodiment of the present invention. The substrate 402 may comprise a semiconductor (e.g., Si), for example. Further, for example, the semiconductor of the substrate 402 may be rendered conductive by doping with an appropriate dopant. As illustrated, the substrate 402 has an insulator layer 404 (for example, a silicon oxide e.g., SiO$_2$)) and a conductor layer 406 (e.g., a metal layer) on a surface of the substrate 402. The insulator layer 404 is disposed between the conductor layer 406 and the substrate 402 and serves to electrically isolate the substrate 402 from the conductor layer 406.

Figure 5B:
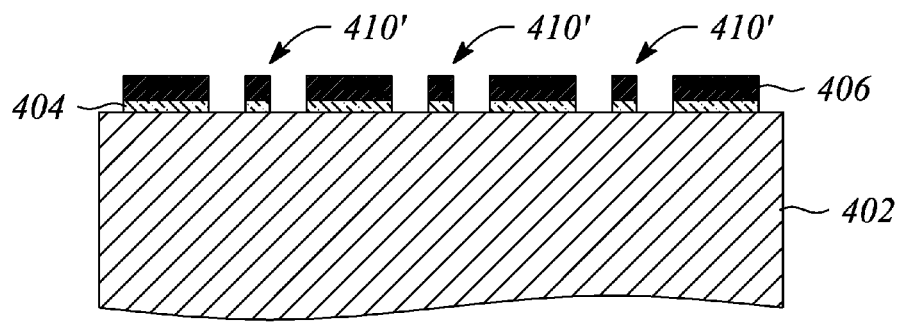
FIG. 5B illustrates a cross sectional view of the substrate in FIG. 5A following patterning of a conductor layer and an insulator layer, according to an embodiment of the present invention.
Figure 5C:
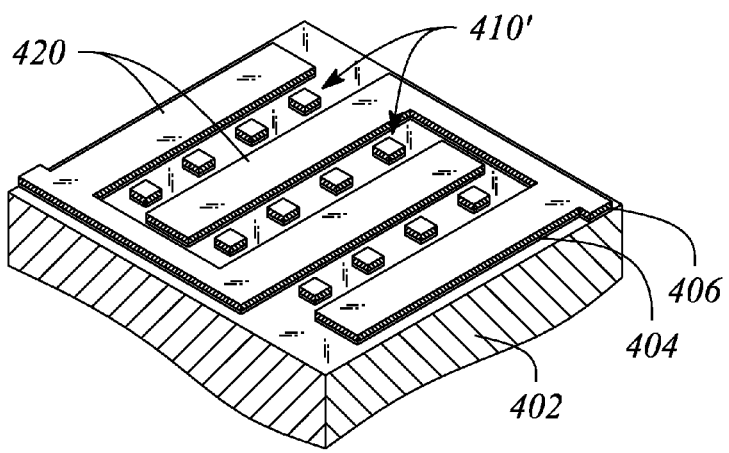
FIG. 5C illustrates a perspective view of the substrate illustrated in FIG. 5B after patterning of the insulator layer and the conductor layer, according to an embodiment of the present invention.

FIG. 5B illustrates a cross sectional view of the substrate 402 of FIG. 5A following patterning of the conductor layer 406 and the insulator layer 404, according to an embodiment of the present invention. FIG. 5C illustrates a perspective view of the substrate 402 illustrated in FIG. 5B after patterning of the insulator and conductor layers 404, 406, according to an embodiment of the present invention. As illustrated, the insulator and conductor layers 404, 406 have been patterned to define eventual locations 410' of a plurality of nano-needles (e.g., as defined by rectangular patches of conductor and insulator). Further, as illustrate in FIG. 5C, the conductor layer 406 has been patterned into a plurality of interdigitated electrodes 420. The electrodes 420 are disposed on either side of a row of the rectangular patches 410' that define the plurality of nano-needles.

Figure 5D:
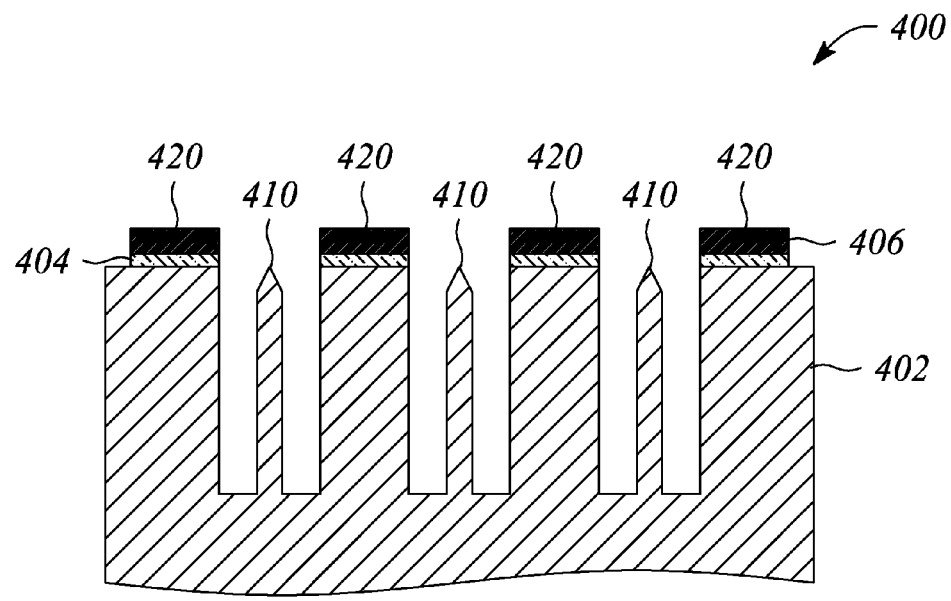
FIG. 5D illustrates a cross sectional view of the vibrating tip SERS apparatus of FIG. 5C following removal of exposed substrate material between rectangular patches that define nano-needles and electrodes, according to an embodiment of the present invention.

FIG. 5D illustrates a cross sectional view of the vibrating tip SERS apparatus 400 of FIG. 5C following removal of exposed substrate material between the rectangular patches 410' (not illustrated in FIG. 5D) that define the nano-needles 410 and the electrodes 420, according to an embodiment of the present invention. For example, a relative deep etch process such as, but not limited to, a Bosch process may be employed to remove the exposed substrate material to produce the result illustrated in FIG. 5D. The removal of the exposed substrate material produces the plurality of nano-needles 410 (i.e., under locations of the rectangular patches 410') between the electrodes 420. Moreover as illustrated in FIG. 5D, the substrate material removal results in the formation of a channel between the electrodes 420 in which the nano-needles 410 are standing. The nano-needles 410 are attached at a bottom of the channel. While the conductor material and the insulator material of the rectangular patches 410' are not illustrated in FIG. 5D, it is noted that these materials may be purposely undercut during a portion of the deep etch process to provide sharp tips to the nano-needles 410, as illustrated in FIG. 5D, and as a consequence, the rectangular patches 410' fall off as a result of the etching process.

In some embodiments, removal of the rectangular patches may occurs as direct consequence of the under cutting used to sharpen the tips of the nano-needles. In other embodiments, the rectangular patches are removed by additional processing (not illustrated). For example, the rectangular patches may be removed by mechanical agitation or relatively vigorous washing with a solvent solution.

Figure 5E:
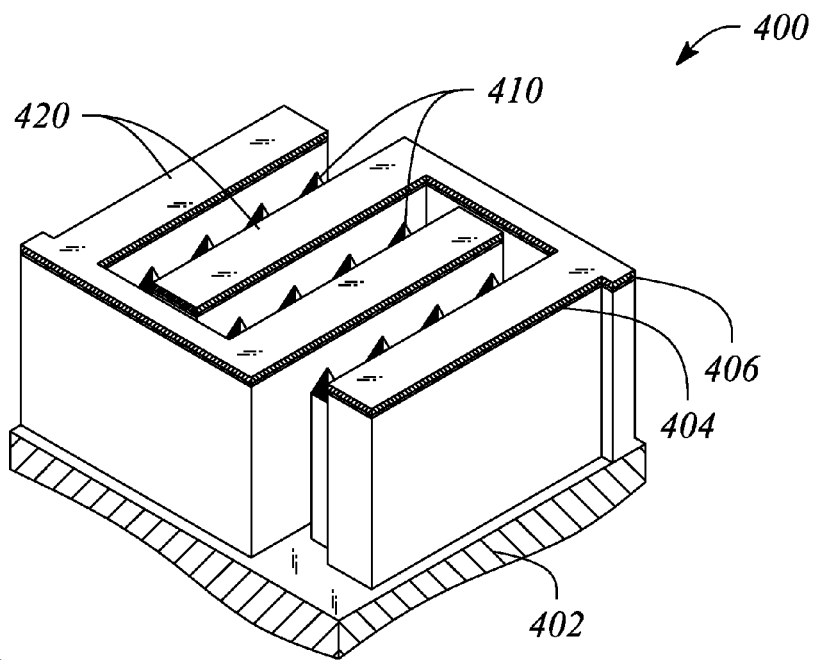
FIG. 5E illustrates a perspective view of the vibrating tip SERS apparatus of FIG. 5D upon completion of fabrication, according to an embodiment of the present invention.

FIG. 5E illustrates a perspective view of the vibrating tip SERS apparatus 400 of FIG. 5D upon completion of fabrication, according to an embodiment of the present invention. Following completion of the vibrating tip SERS apparatus 400, additional processing (not illustrated) may be employed to the apparatus 400. For example, a Raman-active material layer may be applied to the tips of the nano-needles 410. A Raman-active material layer of gold (Au) or silver (Ag) (e.g., Au or Ag nanoparticles) may be sprayed onto the nano-needles 410 or deposited onto the nano-needles 410 using an electrochemical deposition process (e.g., focused ion beam deposition), for example.

Thus, there have been described embodiments of a surface enhanced Raman spectroscopy (SERS) apparatus and (SERS) system and a method of SERS that employ a nano-needle having a vibrating tip. It should be understood that the above-described embodiments are merely illustrative of some of the many specific embodiments that represent the principles of the present invention. Clearly, those skilled in the art can readily devise numerous other arrangements without departing from the scope of the present invention as defined by the following claims.

What is claimed is:

1. A vibrating tip surface enhanced Raman spectroscopy (SERS) apparatus comprising:
   a nano-needle having a tip at a free end opposite an end of the nano-needle that is attached to a substrate, the tip being substantially sharp, the tip being configured to adsorb an analyte; and
   a vibration source configured to provide an alternating current (AC) electric field that induces a vibration of the free end and the tip of the nano-needle,
   wherein the vibration of the nano-needle under the influence of the AC electric field facilitates detection of a Raman scattering signal from the analyte adsorbed on the tip of the nano-needle.

2. The vibrating tip SERS apparatus of claim 1, wherein the nano-needle has a tapered shape, the nano-needle being widest at the end of the nano-needle attached to the substrate, the nano-needle tapering to a substantially sharp point at the tip.

3. The vibrating tip SERS apparatus of claim 2, wherein the tapered shape is conical.

4. The vibrating tip SERS apparatus of claim 1, wherein the nano-needle has a columnar shape, the nano-needle tapering to a substantially sharp point in a vicinity of the tip.

5. The vibrating tip SERS apparatus of claim 4, wherein the columnar shape has a rectangular cross section.

6. The vibrating tip SERS apparatus of claim 1, wherein the tip of the nano-needle comprises a Raman-active material layer that is configured to further enhance Raman scattering from a vicinity of the tip.

7. The vibrating tip SERS apparatus of claim 1, wherein the nano-needle comprises a doped semiconductor.

8. The vibrating tip SERS apparatus of claim 1, wherein the nano-needle comprises a plurality of nano-needles.

9. The vibrating tip SERS apparatus of claim 1, wherein the vibration source comprises a pair of electrodes configured to provide the AC electric field, the nano-needle being disposed between the pair of electrodes.

10. A vibrating tip SERS system comprising the vibrating tip SERS apparatus of claim 1, wherein the system further comprises:
    an illumination source configured to illuminate the tip of the nano-needle; and
    a synchronous detector configured to receive a signal scattered from the tip of the nano-needle, the detector being further configured to be gated at and in cooperation with the AC electric field,
    wherein the gating of the synchronous detector facilitates detection of a Raman scattering signal produced with the illumination source by illumination of the analyte adsorbed on the tip.

11. A vibrating tip surface enhanced Raman spectroscopy (SERS) system comprising:
    a nano-needle disposed between spaced apart electrodes, the nano-needle having a tip at a free end opposite an end of the nano-needle that is rigidly attached to a substrate, the tip being substantially sharp, the tip being configured to adsorb an analyte; and
    a synchronous detector configured to receive a Raman signal from the analyte adsorbed on the tip of the nano-needle,
    wherein the electrodes are configured to cooperatively provide an alternating current (AC) electric field, the provided AC electric field being configured to induce a vibration of the nano-needle tip, and wherein the synchronous detector is configured to be gated cooperatively with the vibration of the nano-needle tip.

12. The vibrating tip SERS system of claim 11, wherein the nano-needle has a tapered shape, the nano-needle being widest at the end of the nano-needle attached to the substrate and tapering to a substantially sharp point at the tip.

13. The vibrating tip SERS system of claim 11, wherein the nano-needle has a columnar shape, the nano-needle tapering to a sharp point in a vicinity of the tip.

14. The vibrating tip SERS system of claim 11, wherein the nano-needle comprises a plurality of nano-needles.

15. The vibrating tip SERS system of claim 11, further comprising an illumination source configured to illuminate the tip of the nano-needle.

16. The vibrating tip SERS system of claim 11, wherein the nano-needle comprises a doped semiconductor, and wherein the tip of the nano-needle comprises a Raman-active material layer coating configured to further enhance a Raman signal emitted by the analyte in a vicinity of the tip.

17. A method of surface enhanced Raman spectroscopy (SERS), the method comprising:
    inducing a vibration of a nano-needle using an alternating current (AC) electric field, the nano-needle having a tip at a free end opposite an end of the nano-needle that is attached to a substrate, the tip being substantially sharp;
    illuminating the vibrating tip of the nano-needle, the illumination producing a Raman signal from an analyte adsorbed on the vibrating tip; and
    detecting the Raman signal using a detector that is synchronized to the induced vibration of the nano-needle.

18. The method of surface enhanced Raman spectroscopy (SERS) of claim 17, wherein inducing a vibration comprises providing a pair of electrodes that provides the AC electric field, the pair of electrodes being disposed on either side of the nano-needle in a vicinity of the tip.

19. The method of surface enhanced Raman spectroscopy (SERS) of claim 17, wherein the nano-needle comprises a tapered shape, the nano-needle being widest at the end of the nano-needle attached to the substrate and tapering to a substantially sharp point at the tip.

20. The method of surface enhanced Raman spectroscopy (SERS) of claim 17, wherein the tip has a Raman-active material layer coating, the Raman-active material layer comprising one or more of gold, silver and copper, and wherein the nano-needle comprises a doped semiconductor.

* * * * *